(12) United States Patent
Vidaurri, Jr. et al.

(10) Patent No.: US 6,437,024 B1
(45) Date of Patent: Aug. 20, 2002

(54) MENTHANOL EXTRACTION OF POLAR ORGANIC COMPOUNDS AND MODIFIER COMPOUNDS FROM POLY(ARYLENE SULFIDE) POLYMER AND OLIGOMER STREAMS

(75) Inventors: Fernando C. Vidaurri, Jr.; James W. Waterman; Jon F. Geibel, all of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/394,727

(22) Filed: Sep. 13, 1999

(51) Int. Cl.$^7$ ............................ C08J 11/00
(52) U.S. Cl. ............ 523/340; 528/381; 528/388; 528/495; 528/499; 528/501
(58) Field of Search ............... 528/381, 388, 528/495, 499, 501; 523/340

(56) References Cited

U.S. PATENT DOCUMENTS

| | | | |
|---|---|---|---|
| 4,786,712 A | 11/1988 | Ostlining et al. | 528/388 |
| 4,895,930 A | 1/1990 | Alfes et al. | 528/499 |
| 4,910,294 A | 3/1990 | Ogata et al. | 528/388 |
| 5,126,430 A | 6/1992 | Senga et al. | 528/388 |
| 5,128,445 A * | 7/1992 | Scoggins et al. | |
| 5,183,538 A * | 2/1993 | Scoggins et al. | |
| 5,241,043 A | 8/1993 | Senga | 528/388 |
| 5,278,283 A * | 1/1994 | Miyoshi et al. | |
| 5,334,701 A * | 8/1994 | Ash et al. | |

FOREIGN PATENT DOCUMENTS

JP 62-177028 * 8/1987

* cited by examiner

Primary Examiner—Robert Dawson
Assistant Examiner—Marc S. Zimmer
(74) Attorney, Agent, or Firm—Hsiang-ning Sun

(57) ABSTRACT

A process is provided to recover at least one modifier compound and at least one polar organic compound from a poly(arylene sulfide) reaction mixture comprising high molecular weight poly(arylene sulfide), low molecular weight poly(arylene sulfide), cyclic and linear poly(arylene sulfide) oligomers, at least one polar organic compound, at least one modifier compound, and an alkali metal halide by-product.

21 Claims, No Drawings

MENTHANOL EXTRACTION OF POLAR ORGANIC COMPOUNDS AND MODIFIER COMPOUNDS FROM POLY(ARYLENE SULFIDE) POLYMER AND OLIGOMER STREAMS

FIELD OF INVENTION

This invention relates to the field of processes utilizing methanol for extracting at least one polar organic compound, hereinafter referred to as "POC", and at least one modifier compound from poly(arylene sulfide) polymer and oligomer streams.

BACKGROUND OF THE INVENTION

The production of poly(arylene sulfide), hereinafter referred to as P(AS), for a variety of industrial and commercial uses has been known for some time. P(AS) is moldable into various articles including, but not limited to, parts, films, and fibers by means of, for example, injection molding and extrusion molding techniques. These articles have utility in a variety of applications where heat and chemical resistance properties are desired. For example, P(AS) can be utilized as a material for preparing electrical and electronic parts and automotive parts.

Generally, high molecular weight P(AS) is prepared by contacting reactants comprising at least one dihalogenated aromatic compound, at least one POC, and at least one sulfur source, at least one base, and at least one modifier compound under polymerization conditions.

There are several problems associated with the current synthesis of P(AS) that cause the production expenses to be high. First, in both quench and flash P(AS) processes, modifiers utilized to synthesize the high molecular weight P(AS) are used once in the process and are not captured and recycled for subsequent use. This constitutes a great expense in the production of P(AS) due to the higher feedstock and waste disposal expense. Secondly, POC utilized in the process can be recovered, but often at a high cost. For example, n-hexanol is often utilized to extract N-methyl-2-pyrrolidone (NMP), a common POC. Operating the hexanol extractor system can require the handling of as much as 30 to 40 pounds of n-hexanol per pound of P(AS) produced causing high equipment and operational costs.

This invention provides a P(AS) process for recovering modifier compound and POC, which can greatly reduce the feedstock and disposal expense compared to current P(AS) processes. As a result of these improvements, the P(AS) produced by this invention has higher purity than that produced from current P(AS) processes.

SUMMARY OF INVENTION

It is an object of this invention to provide a process to recover at least one modifier compound and at least one POC from a quench process reaction mixture or flash process reaction mixture.

It is another object of this invention to provide a process that produces high purity, high molecular weight P(AS) product.

In accordance with one embodiment of the present invention, a process is provided to recover at least one POC and at least one modifier from a quench process reaction mixture comprising high molecular weight P(AS), low molecular weight P(AS), cyclic and linear P(AS) oligomers, at least one POC, at least one modifier compound, and an alkali metal halide by-product.

The process comprises:
1) contacting the quench process reaction mixture with methanol to produce a quench process methanol-rich mixture;
2) separating the quench process methanol-rich mixture to produce a high molecular weight P(AS) product, a recycle mixture, and optionally, a low molecular weight P(AS) stream;
   wherein the recycle mixture comprises methanol, POC, and modifier compound;
   wherein the low molecular weight P(AS) stream comprises low molecular weight P(AS) and cyclic and linear P(AS) oligomers.

In accordance with a second embodiment of this invention, a process is provided to recover at least one POC and at least one modifier from a quench process reaction mixture comprising high molecular weight P(AS), low molecular weight P(AS), cyclic and linear P(AS) oligomers, at least one POC, at least one modifier, and an alkali metal halide by-product. The process comprises:
1) contacting the quench process reaction mixture with at least one POC at a temperature sufficient to dissolve substantially all of the low molecular weight P(AS) and cyclic and linear oligomers to produce a quench process POC-rich mixture;
2) separating the quench process POC-rich mixture to produce a quench process solid stream and a quench process liquid stream;
   wherein the quench process solid stream is in a substantially solid form and comprises high molecular weight P(AS), POC, modifier compound, and alkali metal halide by-product;
   wherein the quench process liquid stream is in a substantially liquid form and comprises substantially all of the low molecular weight P(AS) and cyclic and linear P(AS) oligomers, POC, and modifier compound;
3) contacting the quench process solid stream with methanol to produce a quench process methanol-rich P(AS) product mixture; and
4) separating the quench process methanol-rich P(AS) product mixture to produce a high molecular weight P(AS) product and a recycle mixture;
   wherein the recycle mixture comprises methanol, POC, and modifier compound.

In accordance with a third embodiment of this invention, a process is provided to recover at least one POC and at least one modifier compound from a flash process reaction mixture comprising high molecular weight P(AS), low molecular weight P(AS), cyclic and linear P(AS) oligomers, at least one POC, at least one modifier, and an alkali metal halide by-product.
The process comprises:
1) contacting the flash process reaction mixture with methanol to produce a flash process methanol-rich mixture;
2) separating the flash process methanol-rich mixture to produce a P(AS) stream and a recycle mixture;
   wherein the recycle mixture comprises methanol, POC, and modifier compound.

In accordance with a fourth embodiment of this invention, a process is provided to recover at least one POC and at least one modifier compound from a flash process reaction mixture comprising high molecular weight P(AS), low molecular weight P(AS), cyclic and linear P(AS) oligomers, at least one POC, at least one modifier, and an alkali metal halide by-product.

The process comprises:

1) contacting the flash process reaction mixture with at least one POC at a temperature sufficient to dissolve a majority of the low molecular weight P(AS) and cyclic and linear oligomers to produce a flash process POC-rich mixture;

2) separating the flash process POC-rich mixture to produce a flash process solid stream and a flash process liquid stream;
   wherein the flash process solid stream is in a substantially solid form and comprises insoluble P(AS), the POC, modifier compound, and alkali metal halide by-product;
   wherein the flash process liquid stream is in a substantially liquid form and comprises soluble P(AS) and POC;

3) contacting the flash process solid stream with methanol to produce a flash process methanol-rich P(AS) product mixture; and 4) separating the flash process methanol-rich P(AS) product mixture to produce a high molecular weight P(AS) product and a recycle mixture;
   wherein the recycle mixture comprises methanol, POC, and modifier compound.

DETAILED DESCRIPTION OF INVENTION

Different embodiments of this invention provide processes to recover at least one modifier compound and at least one POC from a P(AS) reaction mixture.

P(AS) reaction mixtures useful in this invention can be produced by any method known in the art. Examples of the reaction mixtures useful in this invention are those prepared according to U.S. Pat. Nos. 3,919,177, 4,038,261, 4,038,262, 4,116,947, 4,282,347 and 4,350,810, the entire disclosures of which are herein incorporated by reference. The U.S. Pat. No. 4,038,261 patent discloses poly(phenylene sulfide).

Generally, reaction mixtures useful in this invention are prepared by contacting a halogenated aromatic compound, at least one POC, at least one sulfur source, at least one base, and at least one modifier compound under polymerization reaction conditions to product high molecular weight P(AS). The use of modifier compounds in the production of high molecular weight P(AS) is disclosed in U.S. Pat. No. 5,334,701, herein incorporated by reference.

As used herein, the term "high molecular weight" or "high molecular weight P(AS)" means all P(AS) molecules having molecular weights high enough to be commercially desirable and useable in an uncured state. Generally, the melt flow of a high molecular weight P(AS) is less than about 3,000 g/10 minutes. As used herein, the term "low molecular weight" or "low molecular weight P(AS)" means all P(AS) molecules having molecular weights too low to be commercially desirable and, thus, not useable in an uncured state. Generally, the melt flow of a low molecular weight P(AS) is greater than about 3,000 g/10 minutes.

Halogenated aromatic compounds suitable for producing reaction mixtures useful in this invention can be represented by the formula

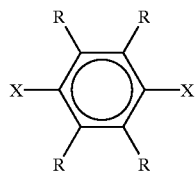

wherein X is a halogen, and R is selected from the group consisting of hydrogen, halogens, and alkyl, cycloalkyl, aryl, alkylaryl, and arylalkyl radicals having from about 6 to about 24 carbon atoms. Exemplary halogenated aromatic compounds include, but are not limited to, p-dichlorobenzene (DCB), p-dibromobenzene, p-diiodobenzene, 1-chloro-4-bromobenzene, 1-chloro-4-iodobenzene, 1-bromo-4-iodobenzene, 2,5-dichlorotoluene, 2,5-dichloro-p-xylene, 1-ethyl-4-isopropyl-2,5-dibromobenzene, 1,2,4,5-tetramethyl-3,6-dichlorobenzene, 1-butyl-4-cyclohexyl-2,5-dibromobenzene, 1-hexyl-3-dodecyl-2,5-dichlorobenzene, 1-octadecyl-2,4-diiodobenzene, 1-chloro-2-phenyl-4-bromobenzene, 1,4-diiodo-2-p-tolylbenzene, 1,4-dibromo-2-benzylbenzene, 1-octyl-4-(3-methylcyclopentyl)-2,5-dichlorobenzene, and mixtures thereof. The preferred halogenated aromatic compound to produce the reaction mixture is DCB, due to availability, ease of use, and high polymerization productivity.

At least one POC must be utilized to produce the reaction mixture. Exemplary POCs include, but are not limited to, cyclic or acyclic organic amides having from about 1 to about 10 carbon atoms per molecule. Exemplary POCs are selected from the group consisting of formamide, acetamide, N-methylformamide, N,N-dimethylformamide, N,N-dimethylacetamide, N-ethylpropionamide, N,N-dipropylbutyramide, 2-pyrrolidone, N-methyl-2-pyrrolidone (NMP), ε-caprolactam, N-methyl-ε-caprolactam, N,N'-ethylenedi-2-pyrrolidone, hexamethylphosphoramide, tetramethylurea, and mixtures thereof. The preferred POC for use in producing the reaction mixture is NMP due to availability and ease of use.

Any suitable source of sulfur can be used to produce the reaction mixture. Exemplary sulfur sources are selected from the group consisting of thiosulfates, substituted and unsubstituted thioureas, cyclic and acyclic thioamides, thiocarbamates, thiocarbonates, trithiocarbonates, organic sulfur-containing compounds selected from mercaptans, mercaptides and sulfides, hydrogen sulfide, phosphorous pentasulfide, carbon disulfides and carbon oxysulfides, and alkali metal sulfides and bisulfides, and mixtures thereof. It generally is preferred to use an alkali metal bisulfide as a source of sulfur wherein the alkali metal is selected from the group consisting of sodium, potassium, lithium, rubidium, and cesium due to availability and ease of use. The preferred alkali metal bisulfide is sodium bisulfide (NaSH) due to availability and low cost.

Suitable bases to produce the reaction mixture are alkali metal hydroxides selected from the group consisting of lithium hydroxide, sodium hydroxide, potassium hydroxide, rubidium hydroxide, cesium hydroxide, and mixtures thereof. If desired, the base can be produced in-situ by reaction of the corresponding oxide with water. The preferred base is sodium hydroxide (NaOH) due to availability and ease of use.

At least one modifier compound is utilized to produce the reaction mixture. The modifier compound is selected from the group consisting of alkali metal carboxylates, alkali metal halides which are soluble in POC, water, and mixtures thereof.

Alkali metal carboxylate modifier compounds can be represented by the formula $R^1$-COOM, where $R^1$ of the modifier compound is a hydrocarbyl radical having from 1 to about 20 carbon atoms and is selected from the group consisting of alkyl, cycloalkyl, and aryl and combinations thereof such as alkylaryl, alkylcycloalkyl, cycloalkylalkyl, arylalkyl, arylcycloalkyl, alkylarylalkyl and alkylcycloalkylalkyl, and M is an alkali metal selected from the group consisting of lithium, sodium, potassium, rubidium and cesium. Preferably, in order to have a more efficient polymerization reaction, $R^1$ is an alkyl radical having from 1 to about 6 carbon atoms or a phenyl radical, and M is lithium or sodium. If desired, the alkali metal carboxylate modifier compound can be employed as a hydrate or as a solution or dispersion in water. If desired, the alkali metal carboxylate modifier compound can be produced in-situ by a reaction of the corresponding carboxylic acid and an alkali metal hydroxide or carbonate.

Suitable alkali metal carboxylate modifier compounds which can be employed to produce the reaction mixture are selected from the group consisting of lithium acetate, sodium acetate, potassium acetate, lithium propionate, sodium propionate, lithium 2-methylpropionate, rubidium butyrate, lithium valerate, sodium valerate, cesium hexanoate, lithium heptanoate, lithium 2-methyloctanoate, potassium dodecanoate, rubidium 4-ethyltetradecanoate, sodium octadecanoate, sodium heneicosanoate, lithium cyclohexanecarboxylate, cesium cyclododecanecarboxylate, sodium 3-methylcyclopentanecarboxylate, potassium cyclohexylacetate, potassium benzoate, lithium benzoate, sodium benzoate, potassium m-toluate, lithium phenylacetate, sodium 4-phenylcyclohexanecarboxylate, potassium p-tolylacetate, lithium 4-ethylcyclohexylacetate, and mixtures thereof. The preferred alkali metal carboxylate modifier compound for use in this invention is sodium acetate (NaOAc) due to availability, low cost, and effectiveness.

Alkali metal halide modifier compounds useful in this invention are those which are soluble in the POC or can be made soluble in a mixture of the POC and another modifier compound. For example, lithium chloride can be useful as the modifier compound, since it is soluble in certain POCs, such as, for example, NMP.

At the termination of the polymerization reaction, the reaction mixture comprises high molecular weight P(AS), low molecular weight P(AS), cyclic and linear P(AS) oligomers, at least one POC, at least one modifier compound, an alkali metal halide by-product, and water. The reaction mixture is in a substantially two-phase liquid form at reaction temperatures. Alkali metal halide by-product is present as a precipitate.

In a first embodiment of this invention, a process is provided to recover at least one POC and at least one modifier from a quench process reaction mixture comprising high molecular weight P(AS), low molecular weight P(AS), cyclic and linear P(AS) oligomers, at least one POC, at least one modifier compound, and an alkali metal halide by-product. In a quench process, the reaction mixture is cooled to a temperature below about 240° C., preferably in a range of 100° C. to 240° C. The quench recovery process is disclosed in U.S. Pat. Nos. 4,415,729 and 5,128,445, both of which are herein incorporated by reference.

The first step of the first embodiment comprises contacting the quench process reaction mixture with methanol to produce a quench process methanol-rich mixture. Methanol must be used to remove a majority of the POC and modifier compound from the quench process reaction mixture.

Generally, the quench process reaction mixture is contacted with methanol at a temperature sufficient to remove a majority of the modifier compound and POC. Preferably, the quench process reaction stream is contacted with methanol at a temperature in a range of about 20° C. to about 50° C. In this temperature range, losses of methanol are minimized. Generally, about 1.5 to about 15 pounds of methanol per pound of P(AS) are used to recover the modifier compound and the POC. Preferably, about 7 to about 11 pounds of methanol per pound of P(AS) are used, and most preferably, 8 to 10 pounds of methanol per pound of P(AS). The preferred ranges are established to adequately and economically remove the modifier compound and POC from the quench process reaction mixture.

Generally, the quench process reaction mixture is contacted with methanol a sufficient number of times to adequately remove a majority of the modifier compound and the POC. Preferably, the quench process reaction mixture is contacted with methanol in at least three repetitions. The quench process reaction mixture can be contacted with methanol by any method known in the art. For example, counter-current washing techniques can be utilized. In counter-current washing, the quench process reaction mixture flows in one direction, and methanol flows in the opposite direction.

The second step of the first embodiment of this invention comprises separating the quench process methanol-rich mixture to produce a high molecular weight P(AS) product, a recycle mixture, and optionally, a low molecular weight P(AS) stream. The recycle mixture comprises methanol, POC, and modifier compound. The low molecular weight P(AS) stream comprises low molecular weight P(AS) and cyclic and linear P(AS) oligomers.

The separation can be accomplished by any process known in the art. For example, such processes can include, but are not limited to, screening, centrifugation, and filtration.

The high molecular weight P(AS) product can be contacted with water to produce a water-washed high molecular weight P(AS) product and an alkali metal halide by-product stream. The alkali metal halide by-product stream comprises water, methanol, and alkali metal halide by-product. The water-washed high molecular weight P(AS) product and alkali metal halide by-product then are separated by any process known in the art. For example, such processes can include, but are not limited to, centrifugation, filtration, and screening.

Various additives can be mixed with the high molecular weight P(AS) product obtained in the present invention. Common additives include, but are not limited to, inorganic fillers (e.g., glass fiber, carbon fiber, titanium oxide, calcium carbonate, etc.) antioxidants, heat stabilizers, ultraviolet absorbents, coloring agents, and mixtures thereof.

If necessary, other polymers such as, for example, polyamides, polysulfones, polycarbonates, polyether sulfones, polyethylene terephthalates, polybutylene terephthalates, polyethylenes, polypropylenes, polytetrafluoroethylenes, polyether ester elastomers, and polyether amide elastomers also can be added.

If desired, the high molecular weight P(AS) product can also be cured by heating at temperatures up to about 480° C. to provide cured products having improved properties and high thermal stability and good chemical resistance.

The recycle mixture can be separated in a first separation zone to yield methanol and a recycle feedstock mixture. The recycle feedstock mixture comprises POC and modifier compound. The first separation zone can comprise any means known in the art to separate the recycle mixture. Preferably, a fractionation column is utilized at sufficient temperatures and pressures to allow substantially all of the methanol to be recovered in one stream and the recycle feedstock mixture to be recovered in a different stream. Both the methanol and recycle feedstock mixture can be reused.

Removal of substantially all of the methanol from the recycle mixture can cause the modifier compound to precipitate. For example, since sodium acetate is not appreciably soluble in NMP, sodium acetate can precipitate when the methanol is removed. Preferably, the separating is conducted in the presence of water in order for the modifier compound to form a solution with water and the POC, so that the solution can be handled more easily. Generally, about 2 to about 10 moles of water per mole of modifier compound are added to adequately form the solution. Preferably, about 3 to about 8 moles of water per mole of modifier compound are added, and most preferably, 4 moles to 6 moles of water per mole of modifier compound are added to adequately form the solution.

The alkali metal halide by-product stream can be separated in a second separation zone to produce methanol and a brine stream, wherein the brine stream comprises water and alkali metal halide by-product. The second separation zone can comprise any means known in the art to separate the alkali metal halide by-product stream. Preferably, a fractionation column is utilized at sufficient temperatures and pressures to allow methanol to be recovered in one stream and the brine to be recovered in a different stream. The methanol can be reused.

In a second embodiment of this invention, another process to recover at least one POC and at least one modifier from a quench process reaction mixture is provided. The first step of the second embodiment comprises contacting the quench process reaction mixture with at least one POC at a temperature sufficient to dissolve substantially all of the low molecular weight P(AS) and cyclic and linear oligomers to produce a quench process POC-rich mixture.

The POC can be any POC previously discussed in this disclosure, and preferably, is NMP due to its availability and ease of use. Generally, the POC is at a temperature in a range of about 100° C. to about 220° C. Preferably, the POC is at a temperature in a range of about 135° C. to about 200° C., most preferably, 150° C. to 175° C. At temperatures below about 135° C., the solubility of low molecular weight P(AS) in POC is significantly lower. At temperatures above 200° C., if NMP is used as the POC, the vapor pressure of NMP can require that the contacting be conducted in a pressure vessel. The higher the temperature of contacting the reaction mixture with the POC, the greater the amount of low molecular weight P(AS) and linear and cyclic oligomers that can be removed from the reaction mixture.

Preferably, sufficient POC can be added during contacting to produce a POC-rich mixture that adequately dissolves the low molecular weight P(AS) and linear and cyclic oligomers. This allows removal of substantially all of the low molecular weight P(AS) and linear and cyclic oligomers from the reaction mixture, thus producing a higher purity high molecular weight P(AS) product. Preferably, about 2 to about 7 moles of POC per mole of P(AS) are added for adequate removal. Most preferably, 3 to 6 moles of POC per mole of P(AS) are used.

Generally, the quench process reaction mixture is contacted with the POC at a temperature sufficient to dissolve substantially all of the low molecular weight P(AS) and cyclic and linear oligomers. The quench process reaction mixture can be contacted with the POC multiple times to further remove the low molecular weight P(AS) and linear and cyclic oligomers.

Contacting times between the quench process reaction mixture and the POC should be sufficient to dissolve substantially all of the low molecular weight P(AS) and cyclic and linear oligomers. Contact times as short as 1 minute can be adequate to remove low molecular weight P(AS) and linear and cyclic oligomers from the quench process reaction mixture.

The second step in the second embodiment comprises separating the quench process POC-rich mixture to produce a quench process solid stream and a quench process liquid stream. The quench process solid stream is in a substantially solid form and comprises the high molecular weight P(AS), the POC, modifier compound, and the alkali metal halide by-product The high molecular weight P(AS) is in a substantially granular form. The quench process liquid stream is in a substantially liquid form and comprises the POC, the modifier compound, and substantially all of the low molecular weight P(AS) and cyclic and linear P(AS) oligomers. The low molecular weight P(AS) is in the form of the solids.

The separation should be completed at a temperature similar to the temperature at which the POC was contacted with the quench process reaction mixture. If the quench process POC-rich mixture is cooled, the low molecular weight P(AS) and linear and cyclic oligomers can precipitate on the high molecular weight P(AS) product, thereby decreasing the efficiency of removal. This separation can be accomplished by any process known in the art. For example, screening can be used.

The third step of the second embodiment comprises contacting the quench process solid stream with methanol to produce a quench process methanol-rich P(AS) product mixture. Methanol must be used to remove a majority of the POC and modifier compound from the quench process solid stream.

Generally, the quench process solid stream is contacted with methanol at a temperature sufficient to remove a majority of the modifier compound and POC. Preferably, the quench process solid stream is contacted with methanol at a temperature in a range of about 20° C. to about 50° C. In this temperature range, losses of methanol are minimized. Generally, about 1.5 to about 15 pounds of methanol per pound of P(AS) are used to recover the modifier compound and the POC. Preferably, about 7 to about 11 pounds of methanol per pound of P(AS) are used, and most preferably, 8 to 10 pounds of methanol per pound of P(AS). The preferred ranges are established to adequately and economically remove the modifier compound and POC from the quench process solid stream.

Generally, the quench process solid stream is contacted with methanol a sufficient number of times to adequately remove a majority of the modifier compound and the POC. Preferably, the quench process solid stream is contacted with methanol in at least three repetitions. The quench process solid stream can be contacted with methanol by any method known in the art. For example, counter-current washing techniques can be utilized. In counter-current washing, the quench process solid stream flows in one direction, and methanol flows in the opposite direction.

The fourth step of the second embodiment comprises separating the quench process methanol-rich P(AS) product mixture to produce a high molecular weight P(AS) product and a recycle mixture. The recycle mixture comprises methanol, POC, and modifier compound.

The recycle mixture can be separated in the first separation zone as discussed previously in this disclosure.

The high molecular weight P(AS) product can be contacted with water to produce a water-washed high molecular weight P(AS) product and an alkali metal halide by-product stream. The alkali metal halide by-product stream can be treated in the second separation zone as discussed previously in this disclosure.

In a third embodiment of this invention, a process is provided to recover methanol, sodium acetate, and POC from the quench process liquid stream. The first step in the third embodiment comprises contacting the quench process liquid stream with methanol to produce a quench process methanol-rich low molecular weight P(AS) mixture. The same conditions as used in contacting the quench process solid stream with methanol can be used.

The second step in the third embodiment comprises separating the quench process methanol-rich low molecular weight P(AS) mixture to produce a low molecular weight P(AS) product and a recycle stream. The recycle stream comprises the methanol, POC, and modifier compound. The low molecular weight P(AS) product comprises the low molecular weight P(AS) and cyclic and linear P(AS) oligomers. The separation can be accomplished by any process known in the art. For example, such processes can include, but are not limited to, centrifugation and filtration.

The recycle mixture can be separated in the first separation zone as discussed previously in this disclosure.

The low molecular weight P(AS) product can be contacted with water to produce a water-washed low molecular weight P(AS) product and an alkali metal halide by-product stream. The alkali metal halide by-product stream can be treated in the second separation zone as discussed previously in this disclosure.

In a fourth embodiment of this invention, a process to recover at least one POC and at least one modifier from a flash process reaction mixture is provided.

In a flash recovery process, the reaction mixture is subjected to low pressure evaporation to remove a majority of the POC. If desired, the POC can be recycled for subsequent polymerizations after condensation. After flash recovery, a flash process reaction mixture is produced comprising high molecular weight PAS, low molecular weight P(AS), cyclic and linear P(AS) oligomers, alkali metal halide by-product, modifier compound, and POC.

Conditions employed during the flash recovery process can vary appreciably but preferably reduced pressures can be employed. Generally, pressure in the flash recovery process should be sufficient to evaporate about 30% to about 90% of the POC, typically, a pressure reduction of approximately 200 psig is required. Pressures as low as 0.05 psig can be employed although the pressure generally is not below one psig. Temperatures of the reaction mixture from the reactor usually range from about 200° C. to about 325° C. Temperatures in a flash recovery vessel after pressure reduction generally range from about 90° C. to about 200° C. depending upon the pressure in the flash recovery vessel.

Various methods of flash recovery of P(AS) are known in the art including U.S. Pat. Nos. 3,478,000 and 3,956,060, both of which are herein incorporated by reference.

The first step of the fourth embodiment comprises contacting the flash process reaction mixture with methanol to produce a flash process methanol-rich mixture. The procedures for contacting the flash process reaction mixture with methanol is the same as discussed previously for the quench process reaction mixture.

The second step of the third embodiment comprises separating the flash process methanol-rich mixture to produce a P(AS) product and a recycle mixture. The recycle mixture comprises methanol, POC, and modifier compound. The P(AS) product comprises high molecular weight P(AS), low molecular weight P(AS), and cyclic and linear P(AS) oligomers. The separation can be accomplished by any process known in the art. For example, such processes can include, but are not limited to, centrifugation and filtration.

The recycle mixture can be separated in the first separation zone as discussed previously in this disclosure.

The P(AS) product can be contacted with water to produce a water-washed P(AS) product and an alkali metal halide by-product stream. The alkali metal halide by-product stream can be treated in the second separation zone as discussed previously in this disclosure.

In a fifth embodiment of this invention, a process is provided to recover at least one POC and at least one modifier compound from a flash process reaction mixture comprising high molecular weight P(AS), low molecular weight P(AS), cyclic and linear P(AS) oligomers, at least one POC, at least one modifier, and an alkali metal halide by-product.

The first step of the fifth embodiment comprises contacting the flash process reaction mixture with at least one POC at a temperature sufficient to dissolve a majority of the low molecular weight P(AS) and cyclic and linear oligomers to produce a flash process POC-rich mixture. The flash process reaction mixture is contacted with POC by the same method discussed previously for the quench process reaction mixture.

The second step of the fifth embodiment comprises separating the flash process POC-rich mixture to produce a flash process solid stream and a flash process liquid stream. The flash process solid stream is in a substantially solid form and comprises insoluble P(AS), the POC, modifier compound, and the alkali metal halide by-product. The flash process liquid stream is in a substantially liquid form and comprises soluble P(AS) and the POC. The separating can be accomplished by any process known in the art. For example, such processes can include, but are not limited to, centrifugation and filtration.

The third step of the fifth embodiment comprises contacting the flash process solid stream with methanol to produce a flash process methanol-rich P(AS) product mixture. The flash process solid stream is contacted with methanol by the same method discussed previously for the quench process solid stream.

The fourth step of the fifth embodiment comprises separating the flash process methanol-rich P(AS) product mixture to produce a high molecular weight P(AS) product and a recycle mixture. The recycle mixture comprises methanol, the POC, and modifier compound. The separation can be accomplished by any process known in the art. For example, such processes can include, but are not limited to, centrifugation and filtration.

The recycle mixture can be separated in the first separation zone as discussed previously in this disclosure.

The high molecular weight P(AS) product can be contacted with water to produce a water-washed high molecular weight P(AS) product and an alkali metal halide by-product stream. The alkali metal halide by-product stream can be treated in the second separation zone as discussed previously in this disclosure.

EXAMPLES

Example 1

The following example shows that methanol can be separated from NMP by fractionation.

75 grams of methanol and 75 grams of NMP (Fisher Purified Grade) were added to a 250 milliliter round bottom flask containing boiling chips. The flask was attached to a vacuum jacketed fractionating column. Heat was applied to the round bottom flask using a heating mantle. The vacuum jacketed fractionating column heated slowly due to internal reflux. A vapor started to flow through a condenser and into a receiver to produce an overhead liquid stream. The flow of vapor slowed until the temperature of the fractionating column increased with further heating of the round bottom flask. Upon reaching the boiling point of NMP, the flow of the overhead liquid stream resumed. Then, the vacuum jacketed fractionating column was cooled to room temperature. Heating of the round bottom flask was then terminated.

Fractions of the overhead liquid stream were collected in small vials. These fractions and a sample of liquid remaining in the round bottom flask were analyzed using gas chromatography. Analyses of the fractions indicated that 99.547% by weight of the overhead liquid stream collected was methanol and 0.453% by weight was NMP. Analysis of the sample of the liquid in the round bottom flask was found to be 100% NMP.

Thus, methanol can be removed efficiently from NMP.

Example 2

This example shows separation of a recycle mixture to produce methanol and a recycle feedstock mixture.

A recycle mixture containing 78.03 wt. % NMP, 15.90 wt. % methanol, and 6.07 wt. % sodium acetate was fed to a laboratory continuous distillation kettle at a continuous rate of 504.20 cm$^3$/hr. A small quantity of NMP was initially added to the kettle. The kettle was heated until the recycle mixture reached reflux at which point the kettle temperature was approximately 210° C., and the temperature throughout the column was about 66–208° C. A methanol stream was recovered through an overhead splitter and routed to an overhead condenser, and then to an overhead receiver. The overhead splitter was set to collect for 0.2 minutes and to discharge to the overhead receiver for 5 seconds. The recycle feedstock mixture was pumped from the kettle at a rate of 87.40 cm$^3$/hr. After approximately one hour, samples were collected of the methanol stream and the recycle feedstock mixture in the bottom of the kettle.

The recycle feedstock mixture and methanol stream were analyzed by gas chromatography. The recycle feedstock mixture contained 99.50 wt. % NMP, 0.29 wt. % methanol, and 0.21 wt. % of other compounds. The methanol stream contained 99.73 wt % methanol, 0.08 wt. % NMP, and 0.19 wt. % other compounds.

During the experiment, it was noted by visual inspection that the sodium acetate accumulated in the bottom of the distillation kettle and column.

This example teaches that methanol can be removed efficiently from sodium acetate and NMP.

Example 3

This example demonstrates that water can be added to a recycle mixture to help prevent the accumulation of sodium acetate in the bottom of the distillation kettle.

The same procedures as disclosed in Example 2 were utilized except the recycle mixture contained 14.60 wt. % methanol, 72.00 wt. % NMP, 4.60 wt. % sodium acetate, and 8.8 wt. % water. The kettle temperature was approximately 190–198° C., and the temperature throughout the column was approximately 68–102° C. The overhead splitter was set to collect for 0.3 minutes and to discharge to the overhead receiver for 5 seconds.

Samples of the methanol stream and the recycled feedstock stream were collected after 8.66 hours of distillation and analyzed by gas chromatography. The recycle feedstock mixture contained 97.53 wt. % NMP, 0.00 wt. % methanol, 1.63 wt. % water, and 0.16 wt. % of other compounds. The methanol stream contained 97.36 wt % methanol, 0.03 wt. % NMP, 2.60 wt. % water, and 0.02 wt. % other compounds. Negligible precipitation of sodium acetate was observed in the bottom of the distillation kettle. Ion chromatograph was used to determine the amount of sodium acetate in the recycle feedstock mixture. 0.69% by weight sodium acetate was found.

This experiment illustrates that the addition of water to the recycle mixture substantially prevents the accumulation of sodium acetate in the bottom of the distillation kettle. An exact mass balance was not achieved in this experiment for the sodium acetate since the distillation was not continued for a long enough duration.

While this invention has been described in detail for the purpose of illustration, it is not intended to be limited thereby but is intended to cover all changes and modifications within the spirit and scope thereof.

What is claimed is:

1. A process to recover at least one polar organic compound and at least one modifier from a quench process reaction mixture comprising high molecular weight poly (arylene sulfide), low molecular weight poly(arylene sulfide), cyclic and linear poly(arylene sulfide) oligomers, at least one polar organic compound, at least one modifier, and an alkali metal halide by-product, said process comprising:
   1) contacting said quench process reaction mixture with additional polar organic compound at a temperature sufficient to dissolve substantially all of said low molecular weight poly(arylene sulfide) and cyclic and linear oligomers to produce a quench process polar organic compound-rich mixture;
   2) separating said quench process polar organic compound-rich mixture to produce a quench process solid stream and a quench process liquid stream;
      wherein said quench process solid stream is in a substantially solid form and comprises said high molecular weight poly(arylene sulfide), polar organic compound, a portion of said modifier compound, and a portion of said alkali metal halide by-product;
      wherein said quench process liquid stream is in a substantially liquid form and comprises substantially all of said low molecular weight poly(arylene sulfide) and cyclic and linear poly(arylene sulfide) oligomers, polar organic compound, and a portion of said modifier compound;
   3) contacting said quench process solid stream with methanol to produce a quench process methanol-rich poly(arylene sulfide) product mixture; and
   4) separating said quench process methanol-rich poly (arylene sulfide) product mixture to produce a high molecular weight poly(arylene sulfide) product and a recycle mixture;
      wherein said recycle mixture comprises methanol, polar organic compound, and modifier compound;
   5) separating said recycle mixture in a first separation zone to yield methanol and a recycle feedstock mixture;
      wherein said recycle feedstock mixture comprises polar organic compound and modifier compound.

2. A process according to claim 1 further comprising contacting said high molecular weight poly(arylene sulfide) product with water to produce a water-washed high molecular weight poly(arylene sulfide) product and an alkali metal halide by-product stream;
   wherein said alkali metal halide by-product stream comprises water, methanol, and a portion of said alkali metal halide by-product.

3. A process according to claim 2 further comprising separating said alkali metal halide by-product stream in a second separation zone to produce methanol and a brine stream;
   wherein said brine stream comprises water and alkali metal halide by-product.

4. A process according to claim 1 wherein said poly(arylene sulfide) is poly(phenylene sulfide) and wherein said at least one polar organic compound and said additional polar organic compounds are NMP.

5. A process according to claim 1 wherein methanol and said recycle feedstock mixture is reused.

6. A process to recover at least one polar organic compound and at least one modifier compound from a flash process reaction mixture comprising high molecular weight poly(arylene sulfide), low molecular weight poly(arylene sulfide), cyclic and linear poly(arylene sulfide) oligomers, at least one polar organic compound, at least one modifier, and an alkali metal halide by-product, said process comprising:
   1) contacting said flash process reaction mixture with additional polar organic compound at a temperature sufficient to dissolve a majority of said low molecular weight poly(arylene sulfide) and cyclic and linear oligomers to produce a flash process polar organic compound-rich mixture;
   2) separating said flash process polar organic compound-rich mixture to produce a flash process solid stream and a flash process liquid stream;
      wherein said flash process solid stream is in a substantially solid form and comprises insoluble poly(arylene sulfide), polar organic compound, a portion of said modifier compound, and a portion of said alkali metal halide by-product;
      wherein said flash process liquid stream is in a substantially liquid form and comprises soluble poly(arylene sulfide) and polar organic compound;
   3) contacting said flash process solid stream with methanol to produce a flash process methanol-rich poly(arylene sulfide) product mixture; and
   4) separating said flash process methanol-rich poly(arylene sulfide) product mixture to produce a high molecular weight poly(arylene sulfide) product and recycle mixture;
      wherein said recycle mixture comprises methanol, polar organic compound, and modifier compound;
   5) separating said recycle mixture in a first separation zone to yield methanol and a recycle feedstock mixture;
      wherein said recycle feedstock mixture comprises polar organic compound and modifier compound.

7. A process according to claim 6 further comprising contacting said high molecular weight poly(arylene sulfide) product with water to produce a water-washed high molecular weight poly(arylene sulfide) product and an alkali metal halide by-product stream;
   wherein said alkali metal halide by-product stream comprises water,
   methanol, and said alkali metal halide by-product.

8. A process according to claim 7 further comprising separating said alkali metal halide by-product stream in a second separation zone to produce methanol and a brine stream;
   wherein said brine stream comprises water and alkali metal halide by-product.

9. A process according to claim 6 further comprising recycling said flash process liquid stream to a poly(arylene sulfide) polymerization process.

10. A process according to claim 6 wherein said separating in said first separation zone is carried out in the presence of water.

11. A process according to claim 6 wherein said poly(arylene sulfide) is poly(phenylene sulfide) and wherein said at least one polar organic compound and said additional polar organic compounds are NMP.

12. A process according to claim 6 wherein methanol and said recycle feedstock mixture is reused.

13. A process to recover at least one polar organic compound and at least one modifier from a quench process reaction mixture comprising high molecular weight poly(arylene sulfide), low molecular weight poly(arylene sulfide), cyclic and linear poly(arylene sulfide) oligomers, at least one polar organic compound, at least one modifier, and an alkali metal halide by-product, said process comprising:
   1) contacting said quench process reaction mixture with additional polar organic compound at a temperature sufficient to dissolve substantially all of said low molecular weight poly(arylene sulfide) and cyclic and linear oligomers to produce a quench process polar organic compound-rich mixture;
   2) separating said quench process polar organic compound-rich mixture to produce a quench process solid stream and a quench process liquid stream;
      wherein said quench process solid stream is in a substantially solid form and comprises said high molecular weight poly(arylene sulfide), polar organic compound, a portion of said modifier compound, and a portion of said alkali metal halide by-product;
      wherein said quench process liquid stream is in a substantially liquid form and comprises substantially all of said low molecular weight poly(arylene sulfide) and cyclic and linear poly(arylene sulfide) oligomers, polar organic compound, a portion of said modifier compound and a portion of said alkali metal halide by-product;
   3) contacting said quench process solid stream with methanol to produce a quench process methanol-rich high molecular weight poly(arylene sulfide) product mixture;
   4) separating said quench process methanol-rich high molecular weight poly(arylene sulfide) product mixture to produce a high molecular weight poly(arylene sulfide) product and a first recycle mixture stream;
      wherein said first recycle mixture stream comprises methanol, polar organic compound, and modifier compound;
   5) contacting said quench process liquid stream with methanol to produce a quench process methanol-rich low molecular weight poly(arylene sulfide) mixture;
   6) separating said quench process methanol-rich low molecular weight poly(arylene sulfide) mixture to produce a low molecular weight poly(arylene sulfide) product and a second recycle mixture stream;
      wherein said second recycle mixture stream comprises methanol, polar organic compound, and modifier compound; and
      wherein said low molecular weight poly(arylene sulfide) product comprises said low molecular weight poly(arylene sulfide) and cyclic and linear poly(arylene sulfide) oligomers;

7) passing said first and said second recycle mixture streams to a first separation zone to yield methanol and a recycle feedstock mixture;
   wherein said recycle feedstock mixture comprises polar organic compound and modifier compound; and 8) contacting said low molecular weight poly(arylene sulfide) product with water to produce a water-washed low molecular weight poly(arylene sulfide) product and a first alkali metal halide by-product stream;
   wherein said alkali metal halide by-product stream comprises water, methanol, and alkali metal halide by-product.

14. A process according to claim 13 further comprising passing said first alkali metal halide by-product stream to a second separation zone to recover said methanol and said alkali metal halide by-product.

15. A process according to claim 14 comprising in addition contacting said high molecular weight poly(arylene sulfide) product with water to produce a water-washed high molecular weight poly(arylene sulfide) product and a second alkali metal halide by-product stream;
   wherein said alkali metal halide by-product stream comprises water, methanol, and alkali metal halide by-product; and
   passing said second alkali metal halide by-product stream to said second separation zone.

16. A process according to claim 13 wherein methanol and said recycle feedstock is reused.

17. A process to recover at least one polar organic compound and at least one modifier from a quench process reaction mixture comprising high molecular weight poly(arylene sulfide), low molecular weight poly(arylene sulfide), cyclic and linear poly(arylene sulfide) oligomers, at least one polar organic compound, at least one modifier, and an alkali metal halide by-product, said process comprising:

1) contacting a quench process reaction mixture with at least one polar organic compound at a temperature sufficient to dissolve substantially all of said low molecular weight poly(arylene sulfide) and cyclic and linear oligomers to produce a quench process polar organic compound-rich mixture;

2) separating said quench process polar organic compound-rich mixture to produce a quench process solid stream and a quench process liquid stream;
   wherein said quench process solid stream is in a substantially solid form and comprises said high molecular weight poly(arylene sulfide), polar organic compound, a portion of said modifier compound, and a portion of said alkali metal halide by-product;
   wherein said quench process liquid stream is in a substantially liquid form and comprises substantially all of said low molecular weight poly(arylene sulfide) and cyclic and linear poly(arylene sulfide) oligomers, polar organic compound, a portion of said modifier compound, and a portion of said alkali metal halide by-product;

3) contacting said quench process liquid stream with methanol to produce a quench process methanol-rich low molecular weight poly(arylene sulfide) mixture;

4) separating said quench process methanol-rich low molecular weight poly(arylene sulfide) mixture to produce a low molecular weight poly(arylene sulfide) product and a recycle mixture stream;
   wherein said recycle mixture stream comprises methanol, polar organic compound, and modifier compound; and
   wherein said low molecular weight poly(arylene sulfide) product comprises said low molecular weight poly(arylene sulfide) and cyclic and linear poly(arylene sulfide) oligomers; and 5) contacting said low molecular weight poly(arylene sulfide) product with water to produce a water-washed low molecular weight poly(arylene sulfide) product and an alkali metal halide by-product stream.

18. A process according to claim 17 wherein said poly(arylene sulfide) is poly(phenylene sulfide) and said polar organic compound is NMP.

19. A process to recover at least one polar organic compound and at least one modifier from a quench process reaction mixture comprising high molecular weight poly(arylene sulfide), low molecular weight poly(arylene sulfide), cyclic and linear poly(arylene sulfide) oligomers, at least one polar organic compound, at least one modifier, and an alkali metal halide by-product, said process comprising:

1) contacting said quench process reaction mixture with additional polar organic compound at a temperature sufficient to dissolve substantially all of said low molecular weight poly(arylene sulfide) and cyclic and linear oligomers to produce a quench process polar organic compound-rich mixture;

2) separating said quench process polar organic compound-rich mixture to produce a quench process solid stream and a quench process liquid stream;
   wherein said quench process solid stream is in a substantially solid form and comprises said high molecular weight poly(arylene sulfide), polar organic compound, a portion of said modifier compound, and a portion of said alkali metal halide by-product;
   wherein said quench process liquid stream is in a substantially liquid form and comprises substantially all of said low molecular weight poly(arylene sulfide) and cyclic and linear poly(arylene sulfide) oligomers, polar organic compound, a portion of said modifier compound, and a portion of said alkali metal halide by-product;

3) contacting said quench process solid stream with methanol to produce a quench process methanol-rich poly(arylene sulfide) product mixture;

4) separating said quench process methanol-rich poly(arylene sulfide) product mixture to produce a high molecular weight poly(arylene sulfide) product and a first recycle mixture stream;
   wherein said first recycle mixture stream comprises methanol, polar organic compound, and modifier compound;

5) contacting said quench process liquid stream with methanol to produce a quench process methanol-rich low molecular weight poly(arylene sulfide) mixture;

6) separating said quench process methanol-rich low molecular weight poly(arylene sulfide) mixture to produce a low molecular weight poly(arylene sulfide) product and a second recycle mixture stream;
   wherein said second recycle mixture stream comprises methanol, polar organic compound, and modifier compound; and
   wherein said low molecular weight poly(arylene sulfide) product comprises said low molecular weight poly(arylene sulfide) and cyclic and linear poly(arylene sulfide) oligomers.

20. A process according to claim 19 further comprising separating said first and second recycle mixture streams in a separation zone to yield methanol and a recycle feedstock mixture.

21. A process according to claim 16 wherein methanol and said recycle feedstock is reused.

* * * * *